US009271923B2

(12) United States Patent
Leek et al.

(10) Patent No.: US 9,271,923 B2
(45) Date of Patent: Mar. 1, 2016

(54) TISSUE REPAIR USING ALLOGENEIC DERMAL FIBROBLASTS

(71) Applicant: Intercytex Limited, Manchester (GB)

(72) Inventors: Mike Leek, Manchester (GB); Paul Kemp, Manchester (GB)

(73) Assignee: INTERCYTEX LIMITED, Manchester (GB)

( * ) Notice: Subject to any disclaimer, the term of this patent is extended or adjusted under 35 U.S.C. 154(b) by 59 days.

(21) Appl. No.: 13/791,177

(22) Filed: Mar. 8, 2013

(65) Prior Publication Data

US 2013/0224158 A1 Aug. 29, 2013

Related U.S. Application Data

(63) Continuation of application No. 11/915,514, filed as application No. PCT/GB2006/001916 on May 25, 2006, now abandoned.

(30) Foreign Application Priority Data

May 26, 2005 (GB) .................................. 0510714.9
Oct. 21, 2005 (GB) .................................. 0521491.1

(51) Int. Cl.
*C12N 5/07* (2010.01)
*A61K 8/98* (2006.01)
*A61L 27/38* (2006.01)
*A61L 27/58* (2006.01)
*A61L 27/60* (2006.01)
*A61Q 19/08* (2006.01)

(52) U.S. Cl.
CPC ............. *A61K 8/981* (2013.01); *A61L 27/3804* (2013.01); *A61L 27/3839* (2013.01); *A61L 27/3895* (2013.01); *A61L 27/58* (2013.01); *A61L 27/60* (2013.01); *A61Q 19/08* (2013.01)

(58) Field of Classification Search
CPC ........................... C12N 5/0625; C12N 5/0656
USPC ................................................. 435/325, 371
See application file for complete search history.

(56) References Cited

U.S. PATENT DOCUMENTS

| | | | |
|---|---|---|---|
| 5,591,444 A | 1/1997 | Boss, Jr. | |
| 5,858,390 A | 1/1999 | Boss, Jr. | |
| 6,124,522 A | 9/2000 | Schroeder | |
| 6,533,819 B1 | 3/2003 | Urry et al. | |
| 6,632,666 B2 | 10/2003 | Baust et al. | |
| 6,699,470 B1 | 3/2004 | Ameer et al. | |
| 6,733,530 B1 | 5/2004 | Lam et al. | |
| 6,878,383 B2 | 4/2005 | Boss, Jr. et al. | |
| 2002/0022883 A1 | 2/2002 | Burg | |
| 2002/0161440 A1 | 10/2002 | Son et al. | |
| 2003/0069639 A1 | 4/2003 | Sander et al. | |
| 2003/0165482 A1 | 9/2003 | Rolland et al. | |
| 2004/0013652 A1* | 1/2004 | Marko et al. ................. 424/93.7 |
| 2004/0029095 A1 | 2/2004 | Lowel et al. | |
| 2004/0082063 A1 | 4/2004 | Deshpande et al. | |
| 2004/0162615 A1 | 8/2004 | Lam et al. | |
| 2005/0025708 A1* | 2/2005 | Vogel et al. ................. 424/9.4 |
| 2005/0043795 A1 | 2/2005 | Hachiya et al. | |

FOREIGN PATENT DOCUMENTS

| | | |
|---|---|---|
| DE | 4127570 A1 | 2/1993 |
| DE | 10116362 A1 | 10/2002 |
| EP | 0242305 A1 | 10/1987 |
| EP | 0344924 A2 | 12/1989 |
| EP | 0989866 A2 | 4/2000 |
| EP | 1137380 A1 | 10/2001 |
| EP | 1184040 A1 | 3/2002 |
| EP | 1358857 A1 | 11/2003 |
| EP | 1375647 A1 | 1/2004 |
| JP | 11510069 B2 | 9/1999 |
| JP | 11343243 A | 12/1999 |
| JP | 2002-520290 A | 7/2002 |
| JP | 2004344506 A | 12/2004 |
| RU | 2023424 C1 | 4/1995 |
| RU | 2273457 C2 | 1/2000 |
| RU | 2195889 C2 | 1/2003 |
| WO | WO-9704720 A1 | 2/1997 |
| WO | WO-9836704 A1 | 8/1998 |
| WO | WO-9915637 A1 | 4/1999 |
| WO | WO-9951164 A1 | 10/1999 |
| WO | WO-0002572 A1 | 1/2000 |
| WO | WO-0132129 A2 | 5/2001 |
| WO | WO-02072113 A1 | 9/2002 |
| WO | WO-03041568 A2 | 5/2003 |
| WO | WO-03084385 A2 | 10/2003 |

OTHER PUBLICATIONS

Van Buskirk et al., "Cryopreservation: It's Not Just About Cell Yield," *Bioprocess Int.* 3:64-66,68, and 70-72, 2005.

(Continued)

*Primary Examiner* — Ruth Davis
(74) *Attorney, Agent, or Firm* — Clark & Elbing LLP

(57) ABSTRACT

The present invention provides a method for the repair of subcutaneous or dermal tissue in a subject, comprising in one aspect the injection of a suspension of allogeneic dermal fibroblasts into the subject. By injecting a suspension of allogeneic cells, the invention provides, for example, long-term augmentation of the subadjacent tissue without the disadvantages that accompany the preparation and/or use of presently available materials such as autologous fibroblasts cells or collagen.

According to a first aspect of the invention there is provided a method for the augmentation of subcutaneous or dermal tissue in a subject, which method comprises the steps of:

(i) providing a suspension of allogeneic dermal fibroblasts; and (ii) injecting an effective volume of the suspension into tissue subadjacent to the subcutaneous or dermal tissue so that the tissue is augmented.

The method is preferably cosmetic.

19 Claims, No Drawings

(56) References Cited

OTHER PUBLICATIONS

Berfield et al., "Insulin-Like Growth Factor I (IGF-I) Induces Unique Effects in the Cytoskeleton of Cultured Rat Glomerulax Mesangial Cells," *J. Histochem. & Cytochem.* 45:583-593, 1997.

Brown et al., "Fibroblast Migration in Fibrin Gel Matrices," *Am. J. Path.* 142:273-283, 1993.

Clark, "Regulation of Fibroplasia in Cutaneous Wound Repair," *Am. J. Med. Sci.* 306:42-48, 1993.

Cullen et al., "The Differential Regulation and Secretion of Proteinases from Fetal and Neonatal Fibroblasts by Growth Factors," *Int. J. Biochem. Cell Biol.* 29:241-250, 1997.

Eckes et al., "Impaired Wound Healing in Embryonic and Adult Mice Lacking Vimentin," *J. Cell Sci.* 113:2455-2462, 2000.

Geesin et al., "Regulation of Collagen Synthesis in Human Dermal Fibroblasts in Contracted Collagen Gels by Ascorbic Acid, Growth Factors, and Inhibitors of Lipid Peroxidation," *Exp. Cell Res.* 206:283-290, 1993.

Hansbrough et al., "Composite Grafts of Human Keratinocytes Grown on a Polyglactin Mesh-Cultured Fibroblast Dermal Substitute Function as a Bilayer Skin Replacement in Full-Thickness Wounds on Athymic Mice," *J. Burn Care & Rehab.* 14:485-494, 1993.

Inokuchi, "Regeneration Medicine of Epidermic Cell," *Igaku No Ayumi* 199:1142-1146, 2001 (Partial Translation).

Kessler et al., "Fibroblasts in Mechanically Stressed Collagen Lattices Assume a 'Synthetic' Phenotype," *J. Biol. Chem.* 276:36575-36585, 2001.

Kessler-Becker et al., "Expression of Pro-Inflammatory Markers by Human Dermal Fibroblasts in a Three-Dimensional Culture Model is Mediated by an Autocrine Interleukin-1 Loop," *Biochem. J.* 379:351-358, 2004.

Meana et al., "Large Surface of Cultured Human Epithelium Obtained on a Dermal Matrix Based on Live Fibroblast-Containing Fibrin Gels," *Burns* 24:621-630, 1998.

Muhart et al., "Behavior of Tissue-Engineered Skin: A Comparison of a Living Skin Equivalent, Autograft, and Occlusive Dressing in Human Donor Sites," *Arch. Dermatol.* 135:913-918, 1999.

Neidert et al., "Enhanced Fibrin Remodeling In Vitro with TGF-β1, Insulin and Plasmin for Improved Tissue-Equivalents," *Biomaterials* 23:3717-3731, 2002.

Neidert et al., "Fibrin as an Alternative Biopolymer to Type I Collagen for Tissue-Equivalent Fabrication," *BED* 50:215-216, 2001.

Sandulache et al., "Impact of Transplanted Fibroblasts on Rabbit Skin Wounds," *Arch. Otolaryngol. Head Neck Surg.* 129:345-350 (2003).

Schäffer et al., "Nitric Oxide, an Autocrine Regulator of Wound Fibroblast Synthetic Function," *J. Immunol.* 158:2375-2381, 1997.

Tuan et al., "In Vitro Fibroplasia: Matrix Contraction, Cell Growth, and Collagen Production of Fibroblasts Cultured in Fibrin Gels," *Exp. Cell Res.* 223:127-134, 1996.

Whiteside et al., "Heterogeneous Synthetic Phenotype of Cloned Scleroderma Fibroblasts May be Due to Aberrant Regulation in the Synthesis of Connective Tissues," *Arth. Rheum.* 31:1221-1229, 1988.

\* cited by examiner

TISSUE REPAIR USING ALLOGENEIC DERMAL FIBROBLASTS

This application is a continuation of U.S. patent application Ser. No. 11/915,514, filed on Feb. 15, 2008, which is a U.S. National Stage of International Application No. PCT/GB2006/001916, filed on May 25, 2006, which claims the benefit of Great Britain Patent Application No. 0521491.1, filed on Oct. 21, 2005, and Great Britain Patent Application No. 0510714.9, filed on May 26, 2005; each of which is hereby incorporated by reference in their entirety.

The present invention relates to the repair of skin and soft tissue defects, including wrinkles, particularly by injecting materials that augment the volume of the dermis or subcutaneous tissue in human subjects.

Injectable materials have been extensively used for correcting skin and soft tissue defects, especially facial soft tissue defects (see review by Homicz & Watson, 2004, Facial Plastic Surgery 20: 21-29). Defects which respond well to injectable augmentation include static facial rhytids of the forehead, glabella, perioral region, and lateral periorbital (crow's feet) area. An advantage of injectable materials over traditional surgical techniques include ease of administration and minimal pain and discomfort for a subject being treated. Treatment can be conducted in an office setting, thereby reducing costs. However, injectable materials are often reabsorbed over time, which means that repeated applications may be need to achieve the desired results. Within the first 72 h after an injection, the treated area may exhibit transient erythema, edema, ecchymosis and induration. Hypersensitivity reactions may also occur, the severity of which depends on the material being injected and the subject's immune system.

Materials used for injection as dermal augmentation include synthetic and biological materials, with the latter being categorised as xenografts (where the donor and the subject are different species), autografts (where the donor and the subject are the same individual), or allografts (where the donor and the subject are different individuals but the same species; also known as homografts).

The development of synthetic materials for repair of skin and soft tissue defects can be traced back to the use of paraffin in the early 1900s for elevation of facial furrows and depressed contours. The development of purified fluid silicone in the 1950s encouraged further interest in tissue augmentation by synthetic materials. Injection of medical-grade fluid silicone provided a means for firming tissue in such a way as to mimic the supple texture of normal tissue. However, there were several problems with injectable silicone, such as unpredictable inflammatory reaction, migration, extrusion, ulceration, silicone granuloma formation, and even organ failure and death in cases of granulomatous hepatitis, pulmonary embolism and silicone pneumonitis. Although still used in various countries around the world, the FDA declared the use of injectable silicone illegal in 1991.

Synthetic materials are considered to be desirable for tissue augmentation due their potential longevity, and other more reliable and promising synthetic materials are available or are being developed. However, longevity may be a problem if a subject is dissatisfied with the cosmetic effects, if there are adverse tissue reactions to the implanted materials, or if a subject wishes to change their appearance due to changes in fashion trends. As of 2004, no injectable synthetic materials were approved by the US Food and Drug Administration (FDA) for dermal augmentation (Homicz & Watson, 2004, supra).

The most widely used dermal filler is the xenograft biological material bovine collagen. Commercial products comprise purified, enzyme-digested collagen (predominantly type I, with less than 5% type III collagen), and are available as ZYDERM and ZYPLAST from Inamed Aesthetics (Santa Barbara, Calif., USA). ZYDERM is processed to remove by enzymatic degradation the C- and N-terminal peptides of bovine collagen, which are immunogenic in human subjects, thereby yielding a material called atelocollagen that can be used in pre-screened nonreactive subjects (see U.S. Pat. No. 3,949,073; U.S. Pat. No. 4,424,208; and U.S. Pat. No. 4,488,911). The ZYDERM products are reported to be prone to loss of volume over time due to absorption by the host. To address this problem, a glutaraldehyde cross-linked atelocollagen called ZYPLAST was developed (see U.S. Pat. No. 4,582,640; and U.S. Pat. No. 4,642,117). However, some investigators report that there is no or little increased persistence of ZYPLAST compared to ZYDERM (Matti & Nicolle, 1990, Aesthetic Plastic Surgery 14: 227-234; Ozgentas et al., 1994, Ann Plastic Surgery 33: 171).

Following two decades of clinical experience and with the advantages of demonstrated safety and reliability, bovine collagen is regarded as the gold standard for tissue augmentation. Disadvantages of bovine collagen include limited duration of effect, and thus the need for multiple treatments, and the potential for allergic reaction.

Hyaluronic acid is a glycosaminoglycan macromolecule found in the native extracellular matrix of connective tissue. The macromolecule is composed of chains of repeating disaccharide units and due to its hydrophobic structure attracts water into the extracellular matrix to provide turgor to connective tissue. Although hyaluronic acid is identical in structure across different species, thereby reducing the possibility of antigenic cross-reactivity in a host, it undergoes local degradation after transplantation. Commercially available products, including the Hylaform range developed by Genzyme Biosurgery and Restylane range developed by Q-Med Corporation (Uppsala, Sweden), are cross-linked gels of hyaluronic acid derivatives from rooster comb (Hylaform) or from a streptococcal fermentation process (Restylane). Although the incidence of hypersensitivity to these hyaluronic acid derivatives appears to be low, subjects are still at some risk of allergic reaction. Furthermore, as with bovine collagen, hyaluronic acid derivatives provide a limited duration of effect.

Materials which have been used in autografts for the repair of skin and soft tissue defects include autologous fat, autologous dermal extracellular matrix extract (Autologen) and autologous dermal fibroblasts (Isolagen). Liposuction techniques developed in the 1970s provided an effective means for harvesting adipose tissue (fat) from a subject which could then be injected back into the subject in the target region. Although autologous fat grafting has the advantage of minimal risk of allergic reaction and bioincompatibility, it requires a donor site on the subject and has an unpredictable resorption rate which means that it is difficult to easily correct skin and soft tissue defects with precision.

Autologen (developed by Collagenesis Corporation, Beverly, Mass., USA) comprises a dermal extracellular matrix isolated from a subject's skin. The subject's skin, once excised, is processed to isolate dermal matrix components including collagen (types I, III and VI), elastin, fibronectin and glycosaminoglycans. A suspension of these components is then used for injection into a subject for soft tissue augmentation. Treatment with Autologen requires a significant volume of a subject's skin to produce the injectable suspension, and repeated injections are often required to maintain the aesthetic effect of the treatment.

U.S. Pat. No. 5,591,444 describes a method for repairing subcutaneous or dermal tissue in a subject by injection of a suspension of autologous dermal fibroblasts ("Isolagen", developed by Isolagen Technologies, Houston, Tex., USA) into the dermis and subcutaneous tissue subadjacent to the defect. The method involves the preparation of autologous cultured dermal fibroblasts from a specimen obtained from the subject and subsequent injection of the fibroblast preparation into the subject. Initial results regarding the longevity of effect of the treatment have been encouraging, and further advantages include minimisation of risk of allergic reaction and bioincompatibility due to the autologous nature of the injected material. Main disadvantages include the requirement for a donor site on the subject, the subsequent expense and time delay in the preparation of cultured dermal fibroblasts, and the inability to store the product. A further disadvantage of the use of autologous cells is that they have not been shown to have a particularly long viability period ("shelf life") after they have been cultured. For example, it is believed that the autologous cells according to U.S. Pat. No. 5,591,444 need to be implanted in the donor patient within about 8 hours after the end of the culture period. This means that it is necessary to arrange the logistics of treatment so that the cultured autologous cells and the donor/patient are available in the same location at the same time.

Subjects not prepared to undergo skin excision procedures may make use of the allogeneic material Dermalogen (Collagenesis Corporation), which is a similar product to Autologen but derived from pooled human cadavers from accredited tissue banks. Although the duration of the cosmetic effect of Dermalogen is reported as better than Zyplast, there is a risk of allergic reaction. An alternative allogeneic product, Cymetra (Life Cell Corporation, Branchburg, N.J., USA), is a micronised form of Alloderm, an acellular freeze-dried dermal graft derived from pooled human cadavers from accredited tissue banks. The longevity of Cymetra tissue augmentation is unclear. For both Dermalogen and Cymetra, there is a risk of disease transmission the pooled human cadaver sources.

In summary, none of the above-mentioned available injectable materials is wholly satisfactory for the purpose of augmenting the subadjacent dermis and soft tissue, and the search for a successful, reliable and cost-effective material continues.

In the field of wound healing, Morimoto et al. (2005; J. Surg. Res 125: 56-67) describe implantation of collagen sponge seeded with guinea pig autologous or allogeneic fibroblasts for the treatment of wounds created on the backs of sample guinea pigs. Collagen sponge seeded with autologous fibroblasts were found to be markedly preferable for wound healing compared with collagen sponge seeded with allogeneic fibroblasts.

The present invention provides an alternative and simplified method for the repair of subcutaneous or dermal tissue in a subject, comprising in one aspect the injection of a suspension of allogeneic dermal fibroblasts into the subject.

By injecting a suspension of allogeneic cells, the invention provides, for example, long-term augmentation of the subadjacent tissue without the disadvantages that accompany the preparation and/or use of presently available materials.

According to a first aspect of the invention there is provided a method for the augmentation of subcutaneous or dermal tissue in a subject, which method comprises the steps of:
(i) providing a suspension of allogeneic dermal fibroblasts; and
(ii) injecting an effective volume of the suspension into tissue subadjacent to the subcutaneous or dermal tissue so that the tissue is augmented.

The method is preferably cosmetic. The method preferably has a long-term effect (for example, longer than 4 to 6 months or a year).

In an alternative aspect of the invention, the allogeneic dermal fibroblasts are applied to the tissue subadjacent to the subcutaneous or dermal tissue by means other than injection. For example, a suspension, gel or clot of allogeneic dermal fibroblasts may be applied topically such as to surface-abraded dermal tissue.

Further aspects of the invention are recited in the accompanying claims.

Typical defects that can be corrected by this present invention include rhytids, stretch marks, depressed scars, cutaneous depressions of non-traumatic origin, scaring from acne vulgaris, and hypoplasia of the lip. The cells that are injected or applied, according to the invention, are allogeneic cells preferably expanded by passage in a cell culture system.

In a preferred embodiment, the engrafted cells are dermal fibroblasts which are derived from the culture of cells obtained from human neonatal foreskin Neonatal-derived dermal fibroblasts are substantially non-immunogenic. Other sources from which dermal fibroblasts can be prepared according to the invention include mammoplasty-derived tissue, abdominoplasty-derived tissue and polydactylism-derived tissue.

The suspension of allogeneic dermal fibroblasts is in one embodiment substantially free of immunogenic proteins.

The present invention is based, in part, on the recognition that it is not essential to use autologous fibroblasts from a subject as described in U.S. Pat. No. 5,591,444 for the repair of skin and soft tissue defects but that, surprisingly, allogeneic cells may be used to stimulate repair of such defects. The findings of the present invention are unexpected, for example, in view of the perceived and known differences in the prior art between the effects of autologous and allogeneic cells when implanted into a subject (see also Morimoto et al., 2005, supra).

The use of allogeneic cells obviates the need to obtain and culture a biopsy specimen taken from a subject several weeks prior to injection, as specified in U.S. Pat. No. 5,591,444. Benefits of the present invention include the ability to prepare and store sufficient quantities of allogeneic cells and have these cells available for rapid treatment of a subject.

The invention can be practiced by injecting any undifferentiated mesenchymal cell that can be expanded in culture. In a preferred embodiment, dermal fibroblasts are injected because they can be readily obtained and expanded and because they are one of cell types normally present in the dermis and subadjacent tissue.

For the manufacture of a Master Cell Bank (MCB), human dermal fibroblasts (HDF) are in one embodiment isolated from a single human neonatal foreskin. The foreskin is washed twice in 30 ml sterile IPA (isolpropyl alcohol) (or 70% ethanol) followed by two washes in growth medium to remove any traces of transport medium. The washed foreskin is mechanically dissected into small pieces. HDF are isolated from the tissue by a series of enzymatic digestion cycles using collagenase B (Roche) at 37° C. then plated at approximately $2 \times 10^4$ cells/cm$^2$ and cultured in either DMEM/10 [(Dulbecco's Modified Eagle's Medium supplemented with bovine serum (10% v/v) and L-Glutamine (2 mM)] or FSFM [DMEM/Hams F12 (3:1 v/v) supplemented with l-glutamine (2 mM), adenine, selenious acid, insulin, hydrocortisone, ethanolamine, o'phosphorylethanolamine, transferrin, tri-iodo-L-thyronine and epidermal growth factor (10 ng/ml)].

Every 3±1 days, cell morphology and level of confluence is assessed using a light microscope. Growth medium is aspirated from all culture vessels then replaced with fresh medium. HDF are maintained in culture until an appropriate confluence is reached.

HDF are subcultured using 0.25% trypsin-EDTA (or animal product free [APF] alternatives such as NOZYME [JRH Biosciences], TRYPLE [Invitrogen], HYQTASE [Pervio], ACCUTASE [Innovative Cell Technologies]) to detach the cells from the culture vessels, which is subsequently neutralised with growth medium. Cells are pelleted at approximately 500×g, resuspended in fresh growth medium then seeded at a density of 2500 cells/cm2.

After 2 passages, HDF are harvested using 0.25% trypsin-EDTA (or alternatives; as above) to detach the cells from the culture vessels, which is subsequently neutralised with growth medium. Cells are pelleted at approximately 500×g, resuspended in fresh growth medium and the total number of viable cells is calculated using a trypan blue exclusion test. The cells are resuspended at a density of $3 \times 10^6$ cells/ml in DMEM supplemented with 10% DMSO (v/v) and 10% bovine serum (v/v) and transferred to sterile 2 ml cryovials (1 ml cell suspension per vial). Vials are cryopreserved using a controlled rate freezer at a rate of 1° C. per minute then immediately transferred to storage in liquid nitrogen refrigerators.

The resulting passage 3 MCB is quarantined until the required testing has been completed, after which the MCB will be qualified for use.

For Working Cell Bank (WCB) manufacture, one vial of passage 3 HDF (derived from fully tested MCB) is thawed rapidly at 37° C. (±1° C.). The cells are then seeded into a single triple flask in 60 ml of DMEM:10 (as described above).

Every 3±1 days, cell morphology and level of confluence is assessed using a light microscope. Growth medium is aspirated from all culture vessels then replaced with fresh medium. HDF are maintained in culture until an appropriate confluence is reached.

Within 7±1 days after seeding, cells are subcultured using 0.25% trypsin-EDTA (or alternatives as above), and a 1:10 split ratio performed. After 2 passages, cells are harvested using 0.25% trypsin-EDTA (or alternatives as above). The total number of viable cells is calculated using a trypan blue exclusion test then the cells are resuspended at a density of 0.5-1×107 cells/ml in DMEM supplemented with 10% DMSO (v/v) and 10% FBS (v/v) and transferred to sterile 2 ml cryovials. Vials are cryopreserved using a THERMO FORMA Controlled Rate Freezer at a rate of 1° C. per minute then immediately transferred to storage in liquid nitrogen refrigerators.

The resulting passage 6 WCB is quarantined until the required testing has been completed, following which the WCB be released for use in product manufacture.

It is also possible according to the invention to use human dermal fibroblasts at passage numbers differing from those given in the preferred embodiment above. Later passage numbers have greater quantities of cells, but cell viability and effectiveness may diminish with increasing passage number.

For the production of a human neonatal foreskin-derived fibroblast suspension ("ICX-RHY"), one or more vials of a p6 working cell bank are thawed at 37° C. (±1° C.) and plated into tissue culture vessels at a density of 2500 cells/cm². The cells are passaged until an appropriate density is required using DMEM supplemented with 10% gamma irradiated bovine serum (v/v) and glutamine (2 mM). The cells are then removed from the tissue culture flasks using 0.25% trypsin-EDTA (or alternatives as described above), and washed extensively in (serum-free) FSFM (or alternatively in a phosphate buffered saline [PBS] or saline solution). The cells are then suspended for injection in an appropriate volume of isotonic saline or alternative delivery medium.

Cells for application (for example, by injection) may be suspended in one or more of the following delivery media:
(i) an isotonic saline solution;
(ii) serum-free medium such as DMEM/F12 (3:1 v/v) or FSFM;
(iii) a serum-containing culture medium such as DMEM/10 or the media given in (ii) supplemented with a serum (for example, bovine serum);
(iv) a solution containing fibrinogen or fibrin (for example, at a final concentration of 0.1-20 mg/ml);
(v) a solution comprising ascorbate and/or thrombin;
(vi) a solution comprising collagen and/or hyaluronic acid; and
(vii) HYPOTHERMOSOL®, preferably HYPOTHERMOSOL® FRS.

HYPOTHERMOSOL®, preferably HYPOTHERMOSOL® FRS (Registered Trade Mark BioLife Solutions, Inc.) is a preservation medium manufactured by BioLife Solutions, Inc. of Owega, N.Y. 13827.

The components of HYPOTHERMOSOL® FRS are shown in Table 1:

TABLE 1

| HYPOTHERMOSOL ® FRS Composition List |
| --- |
| Components |
| Trolox |
| $Na^+$ |
| $K^+$ |
| $Ca^{2+}$ |
| $Mg^{2+}$ |
| $Cl^-$ |
| $H_2PO_4^-$ |
| $HCO_3^-$ |
| HEPES |
| Lactobionate |
| Sucrose |
| Mannitol |
| Glucose |
| Dextran-40 |
| Adenosine |
| Glutathione | pH 7.6
Osmolatiy ~360

It has been found that a disadvantage of the method of U.S. Pat. No. 5,591,444, using autologous dermal fibroblasts, is that the augmentation effect is slow to develop and may not be noticeable to the patient for some time, for example, several weeks.

An advantage of the present invention is that the injection of allogeneic dermal fibroblasts suspended in HYPOTHERMOSOL® can result in a demonstrable augmentation effect within one or two weeks of first administration. Several administrations of the treatment may be required or desired to achieve a full effect. For example, a treatment regime may involve about 3 injections spaced apart by a period of about 1-2 weeks each.

The volume of saline or delivery medium in which the cells are suspended depends upon such factors as the number of fibroblasts the practitioner desires to inject, the size and number of the defects that are to be treated and the urgency of the subject's desire to obtain the results of treatment. The practitioner can thus suspend cells in a larger volume of saline or medium and inject correspondingly fewer cells at each injection site if required.

For example, according to the invention, between $10^4$ and $10^8$, or between $10^6$ and $10^8$, preferably about $1\text{-}5\times10^7$, for example $1\times10^7$ or $4\times10^7$, fibroblasts are injected. For example, according to the invention, a volume of about 1 ml of suspension is injected. A volume of 0.8 ml maybe used.

It has been found that the commercially available product HYPOTHERMOSOL®, particularly HYPOTHERMOSOL® FRS, is useful in preserving the cultured cells in a viable condition prior to administration to a patient. The cultured fibroblast cells are at a state of high metabolic activity and have a high energy demand. Under normal conditions they may tend to suffer apoptosis, particularly when they are suspended in a medium at relatively high cell density. It appears that suspension of the cells in HYPOTHERMOSOL® allows the cells to remain viable and alive for a longer period than would be the case without this medium. Further, whilst cooling of any viable population of cells in a medium would be expected to prolong viability/life; the use of HYPOTHERMOSOL® with cultured fibroblast cells, together with cooling, appears to provide an unexpectedly advantageous preservation effect; this results in an important benefit of elongated "shelf life" for the product.

As a further aspect of the invention it may be advantageous to suspend the cells for injection in cooled HYPOTHERMOSOL® for a period of time prior to injection. For example, cells may be suspended for conditioning in cooled HYPOTHERMOSOL® for at least an hour at about 2° C. to about 8° C. Subsequently the conditioned cells may be maintained cooled until use, or may be allowed to warm before storage before use. A period of cooled conditioning in HYPOTHERMOSOL® appears to provide a benefit of preservation which can continue even if the material is subsequently warmed. The use of uncooled (ie room temperature) HYPOTHERMOSOL® for conditioning is not desirable. By way of example, cells treated according to this aspect of the invention may be stored, and remain viable, for a period of about 10 days at about 2° C. to about 8° C.

Cell suspensions of the invention can be used to treat dermal defects using the same techniques that those skilled in art presently employ to use ZYDERM and ZYPLAST. The cell suspension can be used in place of atelocollagen solutions with the advantages set forth as above. Representative teachings concerning the use of injectable material for augmenting the subadjacent dermis and subcutaneous tissue can be found in the surgical literature (see Gonzales, 1992, Aesthetic Plastic Surgery 16: 231-234; Nicolle, 1985, Aesthetic Plastic Surgery 9: 159-162; & Pieyre, 1985, Aesthetic Plastic Surgery 9: 153-154; which are hereby incorporated by reference in their entirety).

The treatment of fine superficial facial lines, one embodiment of the invention, can be accomplished as follows. The area to be treated is prepped with alcohol and stretched to give a taut surface. A syringe is filled with a cell suspension and fitted with a 30 ga. needle for injection. The needle is inserted into the skin site as superficially as possible; the orientation of the bevel is not critical. An intradermal injection is made by gentle pressure until a slight blanch is seen. Multiple serial injections are made.

In other embodiments the injectate can be placed in the obicularis musculature, to treat hypoplasia of the lip or into the subcutaneous tissue to treat deep subcutaneous defects.

Depending on the target area to be treated and/or the viscosity of the cell suspension, a larger or narrower gauge needle than 30 ga. may be used.

In an alternative embodiment extensive areas of acne scarring can be treated by dermal abrasion to the level of the middle or deep dermis. A fibroblast-containing suspension or a fibroblast-containing gel or a fibroblast-containing clot (for example, as prepared according to Section 4.2 of U.S. Pat. No. 5,591,444, which is hereby incorporated by reference in its entirety) is fashioned so as to cover the abraded surface and applied so that the fibroblast-seeded side of the suspension, gel or clot is juxtaposed to the abraded dermal surface. The applied suspension, gel or clot is then covered with a surgical dressing such as Xeroform, Adaptic or any nonocclusive surgical dressing.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited references are, hereby, incorporated by reference.

The invention claimed is:

1. A method for the augmentation of subcutaneous or dermal tissue in a subject, which method comprises the steps of:
  (i) providing a suspension comprising allogeneic dermal fibroblasts in a preservation medium having a pH of about 7.6, an osmolality of about 360 and comprising the following components: 6-hydroxy-2,5,7,8-tetramethyl-chromane-2-carboxylic acid, $Na^+$, $K^+$, $Ca^{2+}$, $Mg^{2+}$, $Cl^-$, $H_2PO_4^-$, $HCO_3^-$, HEPES, Lactobionate, Sucrose, Mannitol, Glucose, Dextran-40, Adenosine and Glutathione; and
  (ii) injecting an effective volume of the suspension into tissue subadjacent to the subcutaneous or dermal tissue so that the tissue is augmented.

2. The method of claim 1, wherein the method is cosmetic.

3. The method of claim 1, further comprising a step of identifying a defect that is susceptible to amelioration by augmentation of the subadjacent subcutaneous or dermal tissue.

4. The method of claim 3, wherein the defect is a rhytid, stretch mark, a depressed scar, a cutaneous depression of non-traumatic origin or an under-development of the lip.

5. The method of claim 1, in which the fibroblasts are passaged.

6. The method of claim 1, wherein the suspension further comprises fibrin.

7. The method of claim 6, wherein the fibrin is at a final concentration of 0.1 to 20 mg/ml.

8. The method of claim 6, wherein the fibrin is human fibrin.

9. The method of claim 1, wherein the suspension further comprises collagen and/or hyaluronic acid.

10. The method of claim 1, which further comprises the steps of:
  a) obtaining a dermal biopsy from a source allogeneic to the subject;
  b) passaging the dermal fibroblasts from the dermal biopsy in a culture medium comprising between 0.5% and 20% non-human serum, so as to provide dermal fibroblasts substantially free of adipocytes, keratinocytes and extracellular matrix; and c) forming a suspension of the incubated fibroblasts in the preservation medium.

11. The method of claim 10, in which the dermal biopsy is from human neonatal foreskin.

12. The method of claim 10, in which the suspension is formed by scraping the fibroblasts and/or exposing the fibroblasts to a proteolytic enzyme and/or an animal product-free nonenzymatic alternative thereto.

13. The method of claim 1, in which the subject is human.

14. The method of claim 1, wherein between $10^4$ and $10^8$ fibroblasts are injected.

15. The method of claim 1, wherein a volume of about 1 ml of suspension is injected.

16. The method according to claim 1, wherein the fibroblasts are suspended in the preservation medium at a temperature of about 2° C. to about 8° C. for at least one hour prior to injecting.

17. The method of claim 1, wherein between $10^6$ and $10^8$ fibroblasts are injected.

18. The method of claim 1, wherein $1\text{-}5\times 10^7$ fibroblasts are injected.

19. The method of claim 1, wherein $1\text{-}4\times 10^7$ fibroblasts are injected.

* * * * *